United States Patent
Hatamian et al.

(10) Patent No.: US 11,090,449 B2
(45) Date of Patent: *Aug. 17, 2021

(54) SMART INHALER DEVICE WITH AUTOMATED DOSE DELIVERY, MEASUREMENT, AND MANAGEMENT

(71) Applicant: Vivera Pharmaceuticals Inc., Las Vegas, NV (US)

(72) Inventors: Mehdi Hatamian, Mission Viejo, CA (US); Paul Edalat, Newport Beach, CA (US)

(73) Assignee: Vivera Pharmaceuticals Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/106,575

(22) Filed: Aug. 21, 2018

(65) Prior Publication Data

US 2020/0061314 A1 Feb. 27, 2020

(51) Int. Cl.
*A61M 15/00* (2006.01)
*A61M 15/06* (2006.01)
(Continued)

(52) U.S. Cl.
CPC ...... *A61M 15/0066* (2014.02); *A61M 15/008* (2014.02); *A61M 15/0083* (2014.02);
(Continued)

(58) Field of Classification Search
CPC ............. A61M 15/00; A61M 15/0001; A61M 15/0003; A61M 15/0011; A61M 15/0021;
(Continued)

(56) References Cited

U.S. PATENT DOCUMENTS 5,038,769 A * 8/1991 Krauser ................ A61M 15/00
128/203.27
6,737,042 B2 5/2004 Rabinowitz et al.
(Continued)

FOREIGN PATENT DOCUMENTS

WO 2002094234 A1 11/2002
WO 2013028705 A2 2/2013
(Continued)

OTHER PUBLICATIONS

Marc Cohen, Wireless Monitoring/Reward System for Asthma Inhaler Use, , Mar. 2007 , , , National Institutes of Health, Evanston IL.
(Continued)

*Primary Examiner* — Tu A Vo
(74) *Attorney, Agent, or Firm* — Genius Patent APC; Bruce Angus Hare

(57) ABSTRACT

A smart inhaler device includes: a flow pathway having a cartridge receptacle that is able to house a cartridge, flow meter, pump, and vaporizer; a wireless communication module; and at least one sensor that captures identifying information related to the cartridge. A method of providing a measured dose using a smart inhaler device includes: enabling dosing; measuring a provided dose; and disabling dosing. A smart inhaler system includes: a smart inhaler device; a user device; and a server.

8 Claims, 10 Drawing Sheets

(51) Int. Cl.
*A61M 11/04* (2006.01)
*A61M 11/00* (2006.01)

(52) U.S. Cl.
CPC ......... *A61M 11/042* (2014.02); *A61M 15/002* (2014.02); *A61M 15/0003* (2014.02); *A61M 15/0021* (2014.02); *A61M 2205/3334* (2013.01); *A61M 2205/3368* (2013.01); *A61M 2205/3375* (2013.01); *A61M 2205/3553* (2013.01); *A61M 2205/3561* (2013.01); *A61M 2205/3584* (2013.01); *A61M 2205/502* (2013.01); *A61M 2205/583* (2013.01); *A61M 2205/60* (2013.01); *A61M 2205/609* (2013.01); *A61M 2205/6072* (2013.01); *A61M 2205/8206* (2013.01); *A61M 2205/8243* (2013.01)

(58) Field of Classification Search
CPC ............ A61M 16/201; A61M 15/0065; A61M 15/0068; A61M 15/0071; A61M 15/009; A61M 15/0091; A61M 15/06; A61M 15/08; A61M 11/00; A61M 11/02; A61M 11/04; A61M 11/06; A61M 11/08; A61M 2205/502; A61M 2202/04; A61M 2205/3334; A61M 2202/0484; A61M 2205/505; A61M 2205/581; G16H 20/13; H04W 12/084
See application file for complete search history.

(56) References Cited

U.S. PATENT DOCUMENTS

| | | | |
|---|---|---|---|
| 8,550,069 B2 | 10/2013 | Alelov | |
| 2004/0172162 A1 | 9/2004 | Bonney et al. | |
| 2007/0186923 A1* | 8/2007 | Poutiatine | A61J 7/0038 128/200.14 |
| 2007/0240712 A1* | 10/2007 | Fleming | A61M 15/0028 128/203.15 |
| 2008/0011292 A1* | 1/2008 | Sugita | A61M 5/16827 128/200.19 |
| 2008/0164275 A1 | 7/2008 | Poutiatine et al. | |
| 2009/0156952 A1* | 6/2009 | Hunter | A61M 16/024 600/538 |
| 2010/0105735 A1* | 4/2010 | Palmer | A61J 7/0038 514/326 |
| 2010/0305750 A1 | 12/2010 | Conley | |
| 2012/0035760 A1* | 2/2012 | Portney | G16H 20/13 700/231 |
| 2012/0174914 A1* | 7/2012 | Pirshafiey | A61M 11/041 128/200.14 |
| 2013/0197693 A1* | 8/2013 | Kamen | G16H 20/17 700/244 |
| 2013/0220315 A1* | 8/2013 | Conley | A24F 47/008 128/202.21 |
| 2013/0261794 A1* | 10/2013 | Fauci | A61J 7/0076 700/237 |
| 2013/0269694 A1 | 10/2013 | Patton et al. | |
| 2013/0284192 A1 | 10/2013 | Peleg et al. | |
| 2014/0246035 A1* | 9/2014 | Minskoff | A24F 47/008 131/329 |
| 2014/0322682 A1* | 10/2014 | Baym | G09B 5/02 434/219 |
| 2015/0112707 A1* | 4/2015 | Manice | A61M 15/008 705/2 |
| 2015/0122252 A1* | 5/2015 | Frija | A24F 47/008 128/202.21 |
| 2015/0136158 A1* | 5/2015 | Stevens | A24F 47/008 131/329 |
| 2015/0174348 A1 | 6/2015 | Tunnell et al. | |
| 2015/0272220 A1 | 10/2015 | Spinka et al. | |
| 2015/0320116 A1* | 11/2015 | Bleloch | A61M 15/06 219/628 |
| 2016/0089508 A1* | 3/2016 | Smith | A61M 15/06 128/200.16 |
| 2016/0157524 A1* | 6/2016 | Bowen | A24F 47/008 128/200.14 |
| 2016/0309789 A1* | 10/2016 | Thomas, Jr. | A24F 47/008 |
| 2016/0316821 A1* | 11/2016 | Liu | A24F 47/008 |
| 2016/0325055 A1* | 11/2016 | Cameron | A61M 11/005 |
| 2016/0325057 A1 | 11/2016 | Morrison et al. | |
| 2016/0330999 A1* | 11/2016 | Cameron | B01B 1/005 |
| 2016/0331023 A1* | 11/2016 | Cameron | A24F 47/002 |
| 2016/0331026 A1* | 11/2016 | Cameron | A24F 47/002 |
| 2016/0331027 A1* | 11/2016 | Cameron | A24F 47/002 |
| 2016/0331034 A1* | 11/2016 | Cameron | A24F 47/008 |
| 2016/0331035 A1 | 11/2016 | Cameron | |
| 2016/0331036 A1* | 11/2016 | Cameron | H04M 1/7253 |
| 2016/0337362 A1* | 11/2016 | Cameron | H04L 63/10 |
| 2016/0363570 A1* | 12/2016 | Blackley | G01N 33/0006 |
| 2017/0014582 A1 | 1/2017 | Skoda | |
| 2017/0055588 A1* | 3/2017 | Cameron | H05B 3/44 |
| 2017/0095624 A1 | 4/2017 | Davidson et al. | |
| 2017/0099877 A1* | 4/2017 | Worm | A61M 11/042 |
| 2017/0106153 A1 | 4/2017 | Davidson et al. | |
| 2017/0136193 A1* | 5/2017 | Cameron | A61M 11/042 |
| 2017/0136194 A1* | 5/2017 | Cameron | A61M 11/042 |
| 2017/0136196 A1 | 5/2017 | Davidson et al. | |
| 2017/0157343 A1 | 6/2017 | Davidson et al. | |
| 2017/0181474 A1* | 6/2017 | Cameron | A24F 47/008 |
| 2017/0181475 A1* | 6/2017 | Cameron | A24F 47/008 |
| 2017/0182267 A1* | 6/2017 | Cameron | A61M 11/042 |
| 2017/0249433 A1 | 8/2017 | Hagen et al. | |
| 2017/0304563 A1* | 10/2017 | Adelson | A61M 15/06 |
| 2017/0340844 A1 | 11/2017 | Morrison et al. | |
| 2017/0368273 A1* | 12/2017 | Rubin | A61M 11/042 |
| 2018/0020727 A1 | 1/2018 | Hoffman et al. | |
| 2018/0043114 A1* | 2/2018 | Bowen | A61M 15/003 |
| 2018/0110939 A1* | 4/2018 | Lanzkowsky | A61K 9/007 |
| 2018/0168229 A1* | 6/2018 | Mazur | A24F 47/008 |
| 2018/0256835 A1* | 9/2018 | Fornarelli | A61M 15/0083 |
| 2018/0286208 A1* | 10/2018 | Baker | H04W 4/021 |
| 2018/0289907 A1* | 10/2018 | Marmur | A61M 11/001 |
| 2018/0295886 A1* | 10/2018 | Freeman | A24F 47/008 |
| 2018/0369516 A1* | 12/2018 | Adelson | A61M 15/0025 |
| 2019/0134324 A1* | 5/2019 | Rabinowitz | A61M 15/06 |
| 2019/0158938 A1* | 5/2019 | Bowen | A24F 47/008 |
| 2019/0167927 A1* | 6/2019 | Dagnello | A24F 47/008 |
| 2020/0061314 A1 | 2/2020 | Hatamian et al. | |

FOREIGN PATENT DOCUMENTS

| | | |
|---|---|---|
| WO | 2014145218 A2 | 9/2014 |
| WO | 2015148547 A1 | 1/2015 |
| WO | 20160333419 A1 | 3/2016 |
| WO | 2016090303 A1 | 6/2016 |
| WO | 2016092259 A1 | 6/2016 |
| WO | 2016187110 A1 | 11/2016 |
| WO | 2016187111 A1 | 11/2016 |
| WO | 2017005605 A1 | 1/2017 |
| WO | 2017015303 A2 | 1/2017 |
| WO | 2018064377 A1 | 4/2018 |
| WO | 2020041430 A1 | 2/2020 |

OTHER PUBLICATIONS

Mike Marett et al., Fully-Connected Metered Dose Inhaler to Optimize Care of Asthma and COPD, CISION PRWeb, Dec. 2016, , , PRWeb, Edinburgh, Scotland.
My Health Portal, Wireless inhaler that connects patients to doctors, Employee on-line medical health blog, May 2009.

* cited by examiner

SMART INHALER DEVICE WITH AUTOMATED DOSE DELIVERY, MEASUREMENT, AND MANAGEMENT

BACKGROUND

Many substances may be delivered via an inhaler or vaporizer. Such substances may include, for instance, cannabinoids, opioids, nicotine-based solutions, etc. Such substances may be provided for medical and/or recreational use.

Current delivery devices rely on a user to control dosage and various device settings associated with vaporizing or atomizing substances.

In addition, current devices do not monitor (or indicate) consumed amount or other usage data.

Therefore there is a need for an inhaler device that is able to monitor consumption and automatically control dosage.

SUMMARY

Some embodiments may provide a smart inhaler device. The device may be able to dispense various fluid solutions after vaporizing or atomizing such a solution. Dispensed solutions may include, for instance, opioids, cannabinoids, nicotine-based substances, medications, etc.

Some embodiments may include flow meters and/or other measurement elements that are able to quantify an amount of solution that is dispensed. Such devices may provide a measured dose of a vaporized or atomized substance. In this way, users may be able to administer doses in consistent amounts that may match prescriptions or other guidelines associated with use.

Alternatively, such devices may measure an amount of each received dose. Such measurements may allow users to track usage and monitor overall consumption.

Some embodiments of the inhaler device may include various sensors such as cameras, near field communication (NFC) scanners, etc. that may be used to automatically identify cartridges used by the smart inhaler device. In addition, such sensors may include environmental sensors and/or other appropriate sensors that may be relevant to use of the inhaled substance.

The inhaler device may include an output assist blower that may aid in supplying vaporized substance to users that may have medical conditions or other limitations that would otherwise prevent the users from inhaling a full dose or accurately measuring a received dose.

Some embodiments may include a security module that may capture data such as a fingerprint scan or facial photograph in order to compare the captured data to reference data and determine whether a user is authorized to user the inhaler device.

In some embodiments, the inhaler device may include various user interface (UI) elements. Such UI elements may include, for instance, buttons, displays, indicator lights, touchscreens, etc. In addition, the inhaler device may be able to utilize inputs received from an external device (e.g., a smartphone) and/or provide received inputs to such an external device.

The inhaler device may be able to communicate with various user devices (e.g., smartphones, tablets, personal computers, etc.) across wired or wireless channels that may include one or more networks. Such user devices may execute an application associated with some embodiments that may allow a user to register a device, download usage information, adjust device settings, and/or otherwise interact with the inhaler device.

The inhaler and/or user device may upload information to and/or download information from a resource such as a server or remote storage. Such information may include, for instance, usage data, user information, prescription information, usage instructions, etc. In addition, such information may include software updates, operating parameters, and/or other relevant information used by the inhaler or user device.

The collected information may be shared across various platforms with various appropriate users or entities. For instance, a medical practitioner may be able to access usage data associated with a patient. As another example, a clinical study may be supplied with anonymous usage data.

The preceding Summary is intended to serve as a brief introduction to various features of some exemplary embodiments. Other embodiments may be implemented in other specific forms without departing from the scope of the disclosure.

BRIEF DESCRIPTION OF THE SEVERAL VIEWS OF THE DRAWINGS

The novel features of the disclosure are set forth in the appended claims. However, for purpose of explanation, several embodiments are illustrated in the following drawings.

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide an inhaler device with automated dose delivery, measurement, and management.

A first exemplary embodiment provides a smart inhaler device comprising: a flow pathway comprising a cartridge receptacle that is able to house a cartridge, flow meter, pump, and vaporizer; a wireless communication module; and at least one sensor that captures identifying information related to the cartridge.

A second exemplary embodiment provides a method of providing a measured dose using a smart inhaler device, the method comprising: enabling dosing; measuring a provided dose; and disabling dosing.

A third exemplary embodiment provides a smart inhaler system comprising: a smart inhaler device; a user device; and a server.

Several more detailed embodiments are described in the sections below. Section I provides a description of a device architecture of some embodiments. Section II then describes a system architecture of some embodiments. Next, Section III describes methods of operation utilized by some embodiments. Lastly, Section IV describes a computer system which implements some of the embodiments.

I. Device Architecture

Figure 1:
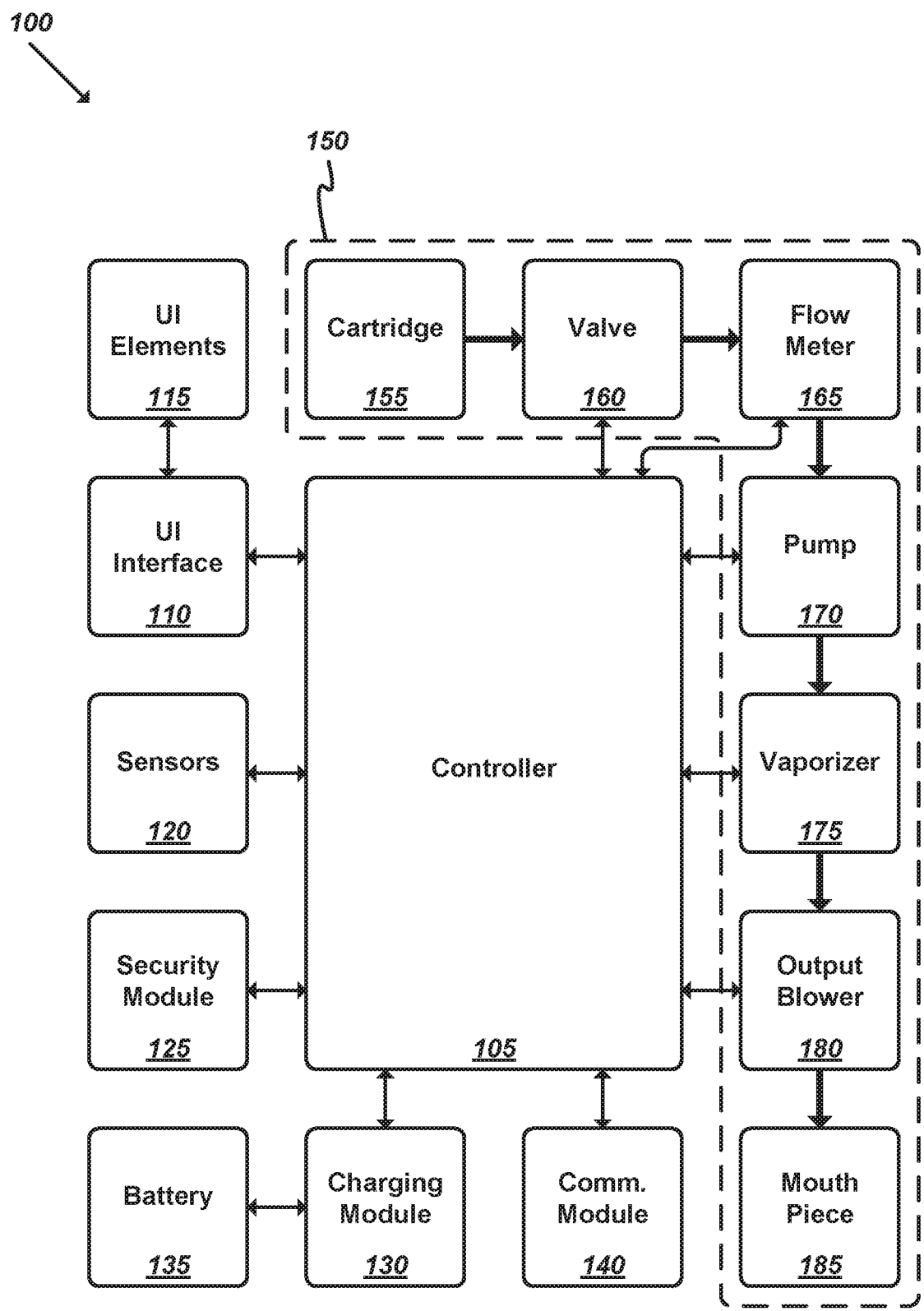
FIG. 1 illustrates a schematic block diagram of an inhaler device according to an exemplary embodiment.

FIG. 1 illustrates a schematic block diagram of an inhaler device 100 according to an exemplary embodiment. As shown, the device may include a controller 105, a user interface (UI) interface 110, various UI elements 115, sensors 120, a security module 125, a charging module 130, a battery 135, a communication module 140, and a substance delivery feature 150.

The controller 105 may include a processor, microcontroller, other appropriate electronic devices, and/or other circuitry that is able to execute instructions and/or otherwise process data. The controller may be able to at least partly direct the operations of other device components. The controller may have an associated storage (not shown) that may be able to store instructions, data, etc.

The UI interface 110 may include various converters, drivers, etc. that are able to receive inputs from the UI elements 115 and/or send outputs to the UI elements. The UI interface 110 may receive outputs from, and send inputs to, the controller 105.

UI elements 115 may include various input and/or output elements. Examples of input elements include buttons, touchscreens, switches, dials, microphones, etc. Examples of output elements include displays, speakers, haptic feedback elements, etc. Some embodiments may include a touchscreen or other appropriate input/output elements. In addition to UI elements included in the device 100, some embodiments may utilize UI elements associated with connected user devices. For instance, a smartphone touchscreen may be used as an input/output element for the device 100. Depending on the size and/or form factor of the device 100, the number of physical UI elements 115 included at the device 100 may be limited. For instance, some embodiments may include a single, multi-function button (e.g., press and hold to dispense the substance, press multiple times in succession to turn on/turn off, etc.). Of course, there is no limitation to appropriate UI elements that may be included (e.g., some embodiments may include a touchscreen, multiple buttons, a keypad, voice input and recognition, etc.).

Sensors 120 may include various electronic components that are able to quantify and/or capture various attributes associated with the device 100 and/or environment. Such sensors may include, for instance, cameras, near field communication (NFC) readers, graphic code readers, temperature sensors, location sensors, movement sensors (e.g., accelerometers), etc. In some embodiments, the sensors 120 may include various components that are able to evaluate received signals (e.g., a bar code reader may utilize a camera to capture an image of the bar code, where the image is evaluated by some associated circuitry in order to extract data encoded in the bar code). The sensors may include various external components (e.g., location information may be retrieved from an associated user device). In some embodiments the sensors may include data retrieved from various network resources (e.g., environmental data such as temperature, humidity, etc. may be retrieved from a weather service based on location rather than measured directly by the device 100).

The security module 125 may manage use of the device 100. The module may interact with the controller 105 in order to identify security criteria associated with an inhaler and/or substance. In addition, the module 125 may utilize data retrieved from sensors 120, UI elements 115, and/or other appropriate components in order to implement various security protocols and/or algorithms. Operation of the security module will be described in more detail in reference to process 400 below.

The battery 135 may be a rechargeable or disposable power source that is able to store and provide power to the various device components. The charging module 130 may provide charging power to the battery 135, distribute power from the battery to other system components, and/or otherwise manage power consumption and/or distribution throughout the device 100. The charging module 130 may include wired (e.g., USB) and/or wireless interfaces (e.g., magnetic or inductive power couplings).

The communication module 140 may allow wired and/or wireless communication between the device 100 and various other appropriate devices and/or systems (e.g., user devices, servers, etc.). The communication module 140 may include various appropriate connectors (e.g., a USB port) and/or wireless pathways (e.g., Bluetooth, radio, etc.).

The substance delivery feature 150 may include a cartridge 155, a valve 160, a flow meter 165, a pump 170, a vaporizer 175, an output blower 180, and a mouth piece 185. Together, such elements may extract the substance from the cartridge 155, vaporize or atomize the extracted substance, and provide the vaporized substance to a user via the mouth piece. The flow pathway 150 may include various different cavities, conduits, etc. that may be arranged in various different ways. For instance, in some embodiments the cartridge 155 and mouth piece 185 may be included in a single element that is able to be attached to device 100.

The cartridge 155 may include a storage cavity for housing a substance, a channel, wick, and/or other appropriate pathway for extracting the substance, a coupling feature such that the cartridge may be able to be attached (and/or detached) from the device 100, and/or other appropriate features. The cartridge 155 may be reusable (i.e., refillable) or disposable. In some embodiments, the cartridge may include various components (e.g., a heating element, an atomizer, etc.) that are able to be controlled and/or otherwise utilized by device 100. The coupling feature may include mechanical elements (e.g., a threaded connector, a compression fit connector, etc.) and/or electronic elements (e.g., contacts, pins, etc.) that are able to engage complementary elements of the device 100.

The cartridge 155 may be removable and thus separate from the device 100. As such, the term "cartridge" may be used through this disclosure to refer to the cartridge 155 itself (i.e., a removable element having a storage cavity) and/or a cartridge receptacle associated with the device 100 (i.e., an attachment point, cavity, or other receptacle that is able to accept a cartridge 155).

The valve 160 may be an electronically controlled flow valve that may be able to either retain a substance within the storage cavity of the cartridge 155 or allow the substance to flow through the delivery feature 150.

The flow meter 165 may include various electronic elements that are able to quantify an amount of cartridge substance that passes the meter. The flow meter may generate a signal that is provided to the controller 105. The controller may analyze the signal in order to determine an amount of substance consumed (e.g., by integrating the received signal).

The pump 170 may be a controllable pump that is able to move the substance along the flow path 150. The controller 105 may be able to define or control various attributes of pump operation (e.g., run time or activation period, speed or strength, etc.). The controller may analyze data received from the flow meter 165 in order to direct the operation of the pump 170. In some embodiments, the flow meter 165 may be omitted and a substance amount may be inferred based on run time (and/or other attributes) of the pump 170.

The vaporizer or atomizer 175 may be able to convert a substance from a liquid state to a gaseous or atomized state. The vaporizer may include various elements such as heating elements, agitation elements, etc. that are able to convert the substance appropriately for inhalation. In some embodiments, the vaporizer may mix the substance with other substances (e.g., air, water, etc.) which may be stored at the cartridge 155 and/or otherwise be available. The vaporizer 175 may be controller by controller 105 such that the vaporizer 175 only operates when the substance is being dispensed.

The output blower 180 may move the vaporized or atomized substance along the flow pathway 150. The output blower 180 may include fans, turbines, and/or other appropriate elements that are able to move the vaporized substance along the path 150. Some embodiments may omit the output blower 180 and/or conditionally operate the blower (e.g., based on user preferences or selections).

The mouth piece 185 may include a conduit and appropriate fixtures that allow the vaporized or atomized substance to be provided to a user for inhalation. The mouth piece may be removable. The mouth piece may be made of various appropriate materials (e.g., metal, plastic, glass, etc.).

Different embodiments may provide different specific device housings and/or other form factor features. For instance, some embodiments may provide a cylindrical vaporizer where device electronics and battery are included at one end of the cylinder and a removable cartridge and mouthpiece may be attached at the opposite end of the cylinder. As another example, some embodiments may include a stationary or "desktop" housing, where elements are included in a box or similar structure that sits on a flat surface during use. Various elements may be attached to, or protrude from, the housing, such as tubes or other conduits, mouth pieces, etc. The housing and/or attachments may include various appropriate materials (e.g., plastic, metal, glass, silicone, rubber, etc.).

During operation, a user may activate the device 100 (e.g., by pressing a button or other UI element 115) and inhale the vaporized substance. The device 100 may store usage information (e.g., amount, time of day, etc.) for provision to other system elements as described below in reference to FIG. 2. Operation of the device 100 will be described in more detail in reference to FIG. 3-FIG. 9 below.

One of ordinary skill in the art will recognize that device 100 may be implemented in various different ways without departing from the scope of the disclosure. For instance, some embodiments may omit various elements (e.g., UI elements, wireless communication elements, etc.). Some embodiments may include additional elements. In addition, the various elements may be arranged in different ways with different communication pathways and/or different flow pathways.

II. System Architecture

Figure 2:
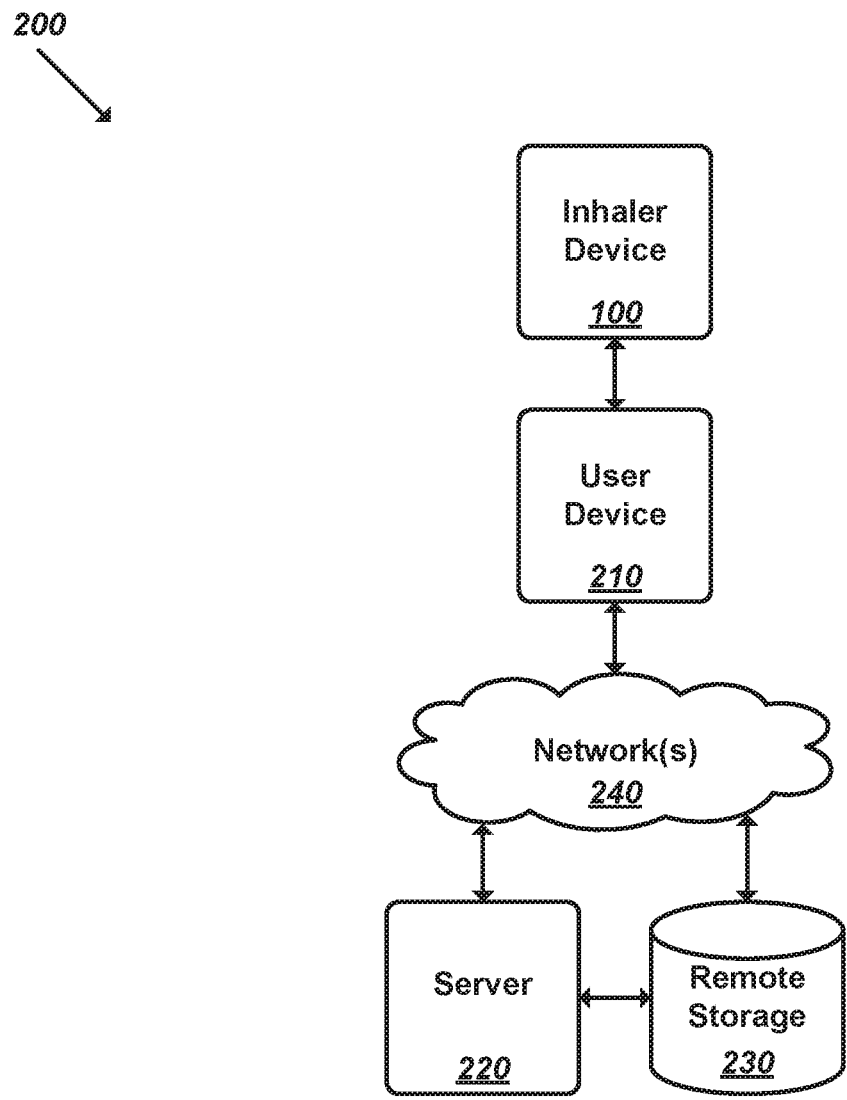
FIG. 2 illustrates a schematic block diagram of a system that includes the inhaler device of FIG. 1.

FIG. 2 illustrates a schematic block diagram of a system 200 that includes the inhaler device 100. As shown, the system 200 may include the inhaler device 100 described above, one or more user devices 210, one or more servers 220, one or more remote storages 230, and a set of networks 240.

Each user device 210 may be an electronic device such as a smartphone, tablet, personal computer, wearable device, medical device or terminal, etc. The user device may be able to be communicatively coupled to the inhaler device 100 (e.g., using module 140) via a wired or wireless channel. The user device 210 may be able to connect to various networks 240. In some embodiments, the inhaler device 100 may be able to connect directly to networks 240 without any user device 210.

Each server 220 may be an electronic device capable of executing instructions and/or otherwise processing data. Servers may be associated with various types of entities or users. For instance, a cartridge manufacturer may have a server that is able to provide information related to cartridges and/or collect information related to use. As another example, a group of medical practitioners such as doctors, nurses, administrators, etc. may be associated with an entity such as a hospital or health care network that maintains a server related to patients or clients of the entity.

As still another example, a server may be associated with a platform or other appropriate resource that is able to link various users and/or groups of users. For instance, a patient user may be able to create an account, collect usage data associated with the account, and provide the data to various other parties (e.g., a doctor, pharmacist, etc.). Such data may be provided anonymously, as appropriate, for use in various studies, trials, etc.

Each remote storage 230 may be an electronic device that is able to store instructions and/or data. Such a storage may be accessed via an associated server 220 or via a resource such as an application programming interface (API). The storages 230 may be able to receive data from the various other system resources and/or provide data to those resources, as appropriate.

The set of networks 240 may include various wired and/or wireless communication pathways, such as Ethernet, cellular networks, Wi-Fi networks, the Internet, etc.

One of ordinary skill in the art will recognize that system 200 may be implemented in various different ways without departing from the scope of the disclosure. For instance, some embodiments may omit various components (e.g., remote storages, servers, etc.). Some embodiments may include additional elements (e.g., external charging devices). In addition, the various elements may be arranged in different ways with different communication pathways.

III. Methods of Operation

Figure 3:
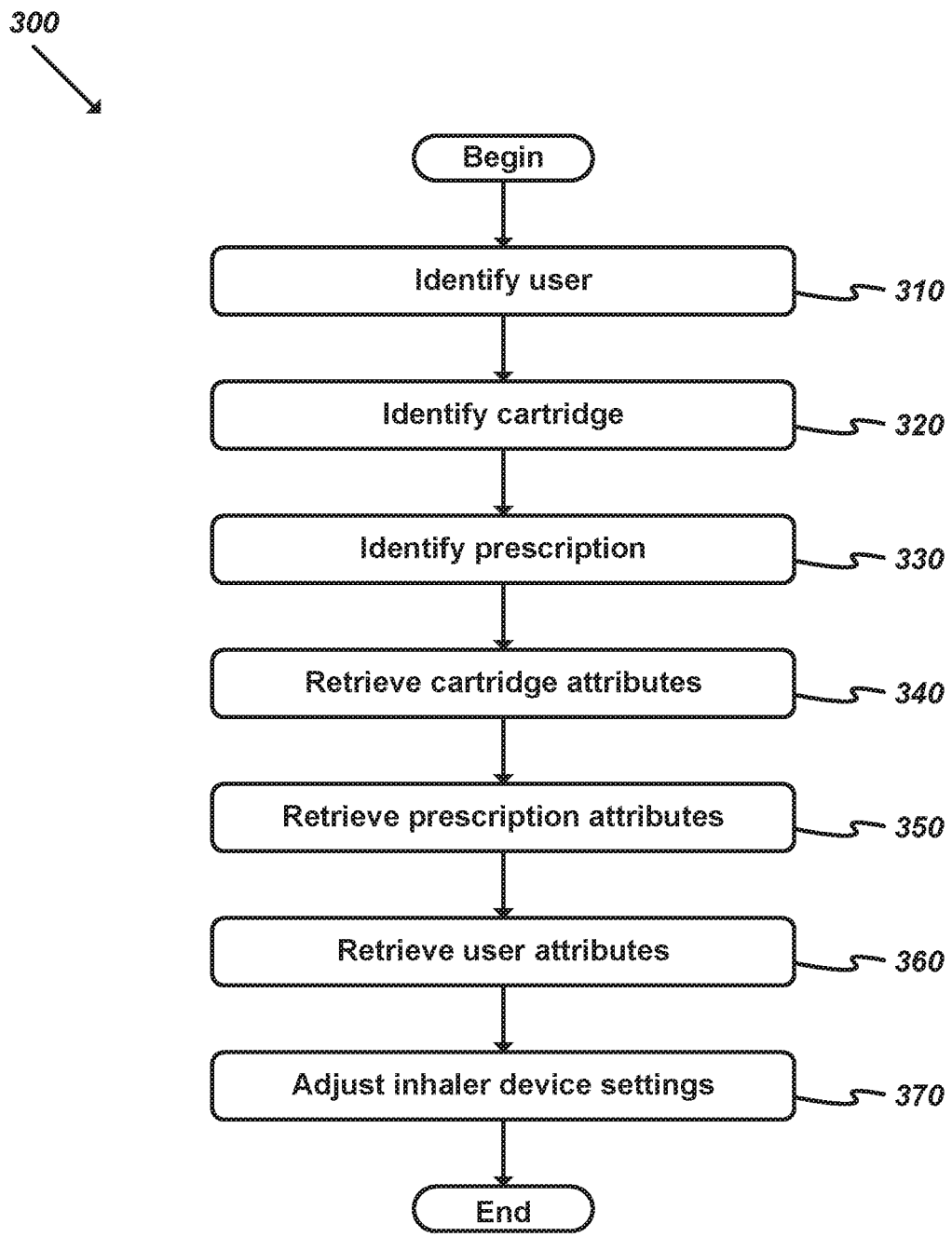
FIG. 3 illustrates a flow chart of an exemplary process that initializes the inhaler device of FIG. 1.

FIG. 3 illustrates a flow chart of an exemplary process 300 that initializes the inhaler device 100. Such a process may be executed by the inhaler device in some embodiments. In addition, various operations may be performed by a resource such as user device 210 or server 220, where such resources may execute applications associated with the device of some embodiments. The process may begin, for instance, when an inhaler device is powered on, when a new cartridge is coupled to the device, after a user reset, after the battery is charged, etc.

As shown, the process may identify (at 310) a user of the device 100. The user may be identified in various appropriate ways, depending on the circumstances. For instance, the device may have been previously associated with a user account using an application of some embodiments. Such account data may be stored at the device itself and/or retrieved from an external resource such as a user device or server. As another example, the first time a device is powered on or otherwise used, the user may be prompted to enter identifying information (e.g., name, username, etc.) that may be used to identify the user in the future. As still another example, some usage may be anonymous and no user information may be identified or otherwise procured.

Next, the process may identify (at 320) the cartridge 155. Such identification may include attributes such as a cartridge type, serial number, etc. The identification may utilize sensors 120. Different embodiments may use different identification algorithms and/or features. For instance, some embodiments may include NFC tags and readers. As another example, some embodiments may utilize graphic codes and optical devices (e.g., cameras, bar code readers, scanners, etc.). In some embodiments, a resource external to the device 100 may be utilized. For instance, a camera included in a user device 210 may be used to scan a graphic code. An application running on the user device may decode the scanned information and identify the cartridge. As another example, an application running on the user device may provide a list of options and a user may select the appropriate cartridge. As still another example, the cartridge 155 may include circuitry that may be read by the device 100 to retrieve a serial number, type, and/or other identifying information. As above, in some usage scenarios, the cartridge may not be identified.

Process 300 may then identify (at 330) a prescription associated with the user and/or cartridge, if appropriate. The prescription may be identified via an external resource such as user device 210, server 220, and/or storage 230. For instance, a request may be sent from the device, via the user device 210 to a server 220. The request may include information associated with the user and/or cartridge. A response may include a serial number or other identifying information related to the prescription. In some embodiments, user inputs may be received that indicate usage is related to a prescription (or that usage is not associated with a prescription).

Next, the process may retrieve (at 340) attributes associated with the cartridge identified at 320. Such attributes may include identifying information (e.g., type, serial number, etc.), usage information (e.g., environmental limitations, vaporizing attributes such as temperature, voltage or current range, etc.), substance information (e.g., volume, concentration, etc.), security information (e.g., prescription requirements, age or demographic requirements, etc.), and/or other appropriate information. If no cartridge was identified (at 320), various default attributes may be used.

The process may then retrieve (at 350) prescription attributes, if a prescription was identified. Such prescription attributes (and/or other usage instructions) may include, for instance, dose amount, dose frequency, maximum dose, maximum dose over time, total usage period, etc. In some embodiments, the prescription attributes may be manually entered by a user.

Process 300 may then retrieve (at 360) attributes associated with the user. Such attributes may include, for instance, biometric information (e.g., age, gender, height, weight, etc.), condition information, user preferences, etc. As above, such attributes may be entered manually. If no user-specific information is available, default values may be used.

Next, the process may adjust (at 370) inhaler settings based on the retrieved data and then may end. Such adjustments may include storage of parameter values at the inhaler device 100. The settings may be related to any module (or set of modules) described above in reference to FIG. 1.

Figure 4:
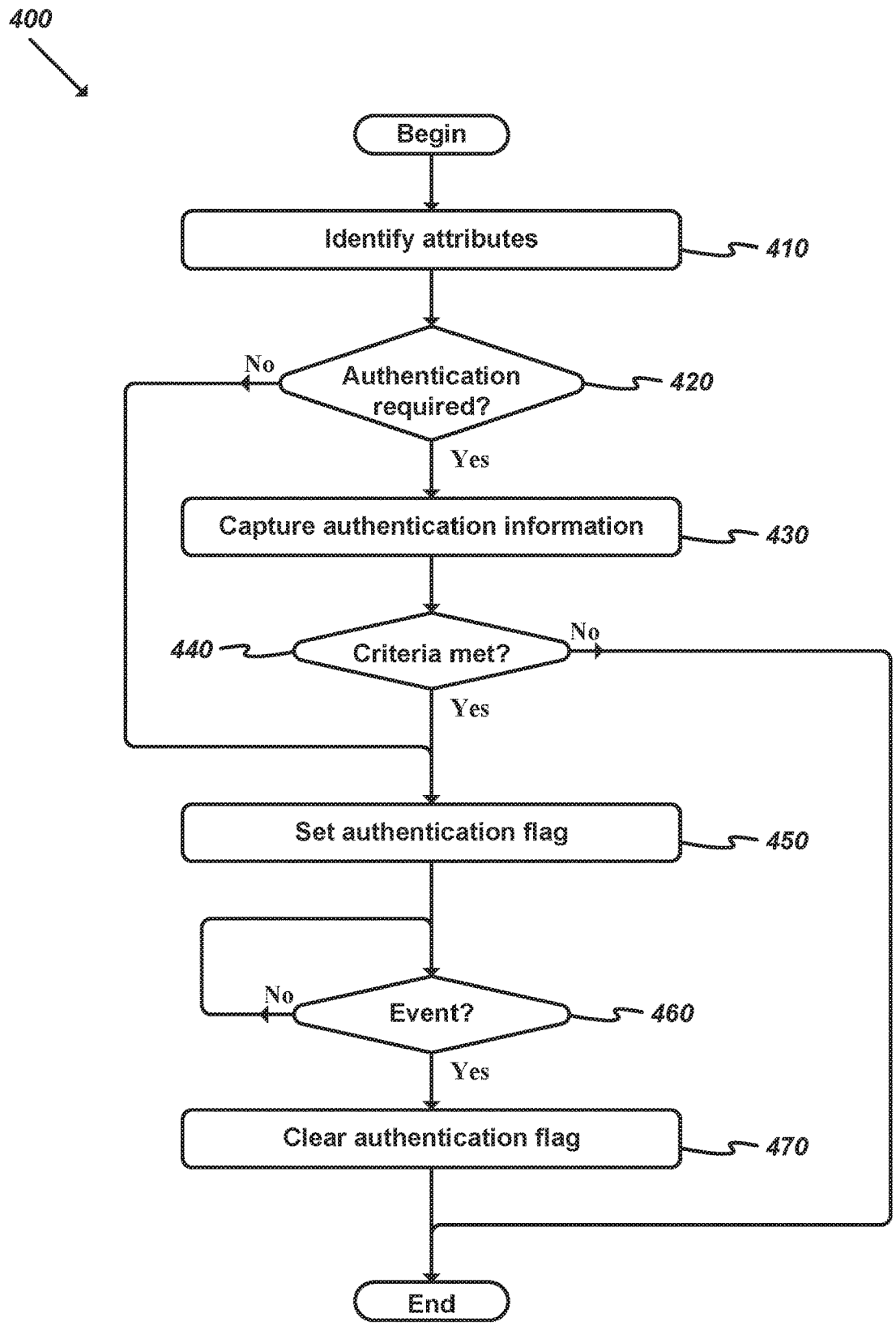
FIG. 4 illustrates a flow chart of an exemplary process that authenticates a device user.

FIG. 4 illustrates a flow chart of an exemplary process 400 that authenticates a device user. Such a process may be executed by the inhaler device 100 in some embodiments. The process may begin, for instance, when a UI element is activated (e.g., a button push is detected), when the device is powered on, etc.

As shown, the process may identify (at 410) various usage attributes associated with the device 100, cartridge 155, user, etc. Such attributes may be retrieved and stored at the device 100 using a process such as a process 300.

Next, the process may determine (at 420) whether authentication is required. Such a determination may be made based on various relevant factors (e.g., cartridge type, substance type, whether the cartridge is associated with a prescription, user settings, etc.).

If the process determines (at 420) that authentication is required, the process may capture (at 430) authentication information. Such information may be captured using various appropriate resources (e.g., UI elements 115, sensors 120, a camera or scanner associated with user device 210, etc.). Captured authentication information may include, for instance, fingerprint scans, photographs of facial features, personal identification number (PIN) or password, etc. Authentication information may be dependent on capabilities of the device 100 and/or whether the device is communicatively coupled to an external resource such as user device 210 or server 220. For instance, if the device 100 includes a single control button, the "password" may include a particular cadence of clicks (e.g., four clicks in a row).

Next, the process may determine (at 440) whether the authentication criteria have been met. Such a determination may be made, for instance, based on matching between a captured fingerprint and previously captured data, facial recognition analysis, voice recognition analysis, etc.

After determining (at 440) that the criteria was met or determining (at 420) that no authentication is required, the process may set (at 450) an authentication flag indicating that use is permitted. Depending on the circumstances, such a flag may be set by default (e.g., for adult use of non-prescription substances).

Next, the process may determine (at 460) whether a security event has occurred. Such events may be defined using various appropriate criteria. For instance, some embodiments may include an authentication timeout such that use has to be re-authenticated after some specified time period. As another example, some embodiments may require re-authorization for each dose to be dispensed. As still another example, some embodiments may require re-authorization if a link to a user device is broken (e.g., indicating that the inhaler 100 has exceeded a specified distance from the user device 210). Some embodiments may monitor device position and/or movement using sensors 120 in order to determine whether a user has put down the device 100 or otherwise ceased use. Other types of events may include environmental events. For instance, some embodiments may include a thermometer and may indicate that a cartridge is no longer usable if it has been exposed to temperatures outside a specified range. As another example, such events may include comparison of current date and time to a specified expiration of the cartridge.

Some embodiments may utilize a continuous identification algorithm. If a continuous identification mode is enabled, the device 100 may require, for instance, continuous finger print detection during use, where such detection may be provided via a dedicated scanner or other appropriate interface element. Such a mode may prevent non-authorized use of the substance provided by the inhaler device. Although a user may be able to circumvent such protection by holding the device for another person, such an approach requires knowledge of the authorized user, thus still providing a deterrent effect.

If the process determines (at 460) that no event has been identified, the process may repeat operation 460 (i.e., the authorization flag may remain set) until the process determines (at 460) that an event has been identified. If the process determines (at 460) that an event has been identified, the process may clear (at 470) the authorization flag and then may end.

Process 400 may be executed as a background process such that any security event identified at 460 causes the authentication flag to be cleared, thus requiring authentication for further use.

Figure 5:
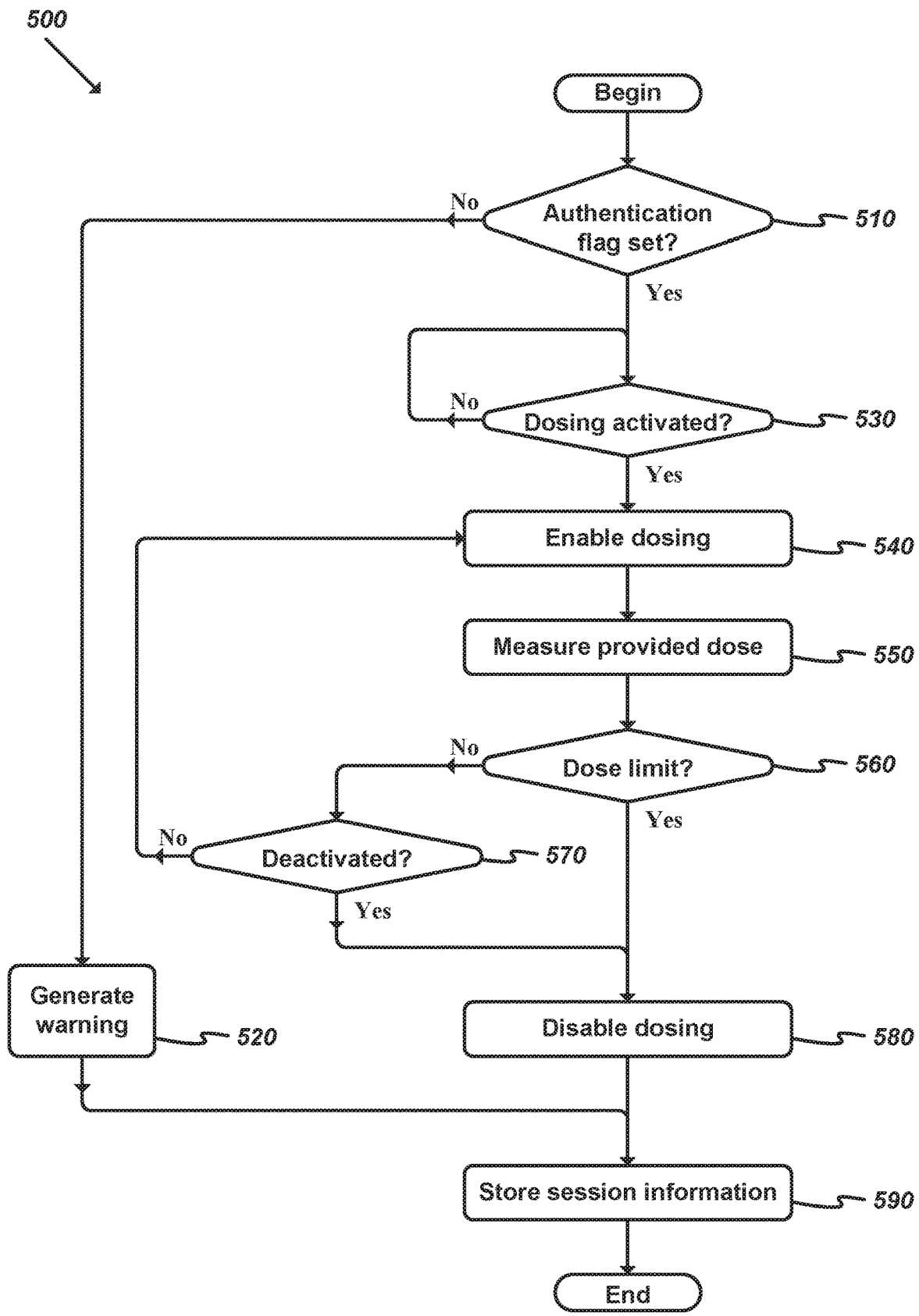
FIG. 5 illustrates a flow chart of an exemplary process that provides an inhaled substance using the inhaler device of FIG. 1.

FIG. 5 illustrates a flow chart of an exemplary process 500 that provides an inhaled substance using the inhaler device 100. Such a process may be executed by the inhaler device in some embodiments. The process may begin, for instance, when a UI element is activated (e.g., a button push is detected), when the device is powered on, etc.

As shown, the process may determine (at 510) whether the authentication flag has been set. If the process determines (at 510) that the flag has not been set, the process may generate (at 520) a warning or error message. Such a message may be indicated at the device 100 (e.g., using a display, haptic feedback element, and/or other UI element 115) or via an external resource such as a user device 210. The message may include an indication of actions required to authenticate use (e.g., scan fingerprint, capture facial photo, enter PIN or password, etc.).

If the process determines (at 510) that the authentication flag has been set, the process may determine (at 530) whether dosing has been activated. Such a determination may be made based on received inputs at the device 100 and/or other appropriate criteria. For instance, in some embodiments, a user may press and hold a button to dispense the substance. If the process determines (at 530) that dosing has not been activated, the process may repeat operation 530 until the process determines (at 530) that dosing has been activated.

If the process determines (at 530) that dosing has been activated, the process may enable (at 540) dosing. Dosing may be enabled in various appropriate ways. One example is described in reference to process 600 below.

Process 500 may then measure (at 550) the provided dose. Such measurement may be made by a resource such as flow meter 165.

Next, the process may determine (at 560) whether there is a dose limit associated with the usage scenario. Such a dose limit may be associated with a cartridge, substance, prescription, user, etc. The dose limit may be associated with a single dispensed dose and/or usage over a period of time. If the process determines (at 560) that there is no dose limit or that the dose limit has not been exceeded, the process may determine (at 570) whether dosing has been deactivated. Such a determination may be made based on various relevant criteria (e.g., whether a button has been released, whether a temperature or other usage threshold has been exceeded, whether a maximum dose time has been exceeded, etc.).

If the process determines (at 570) that dosing has not been deactivated, the process may repeat operations 540-570 until the process determines (at 560) that the dose limit has been reached or determines (at 570) that dosing has been deactivated. A dose limit may be a threshold value where the measured provided dose must meet or exceed the threshold value in order to constitute administration of a full dose.

If the process determines (at 560) that the dose limit has been reached or determines (at 570) that dosing has been deactivated, the process may disable (at 580) dosing. Dosing may be disabled in various appropriate ways. One example is described in reference to process 700 below.

After disabling (at 580) dosing, or after generating (at 520) the warning, the process may store (at 590) session information and then may end. Such information may include, for instance, number of doses, total amount consumed, dose times and durations, authentication information, etc. The stored information may be provided to external resources such as user device 210, server 220, or storage 230.

Figure 6:
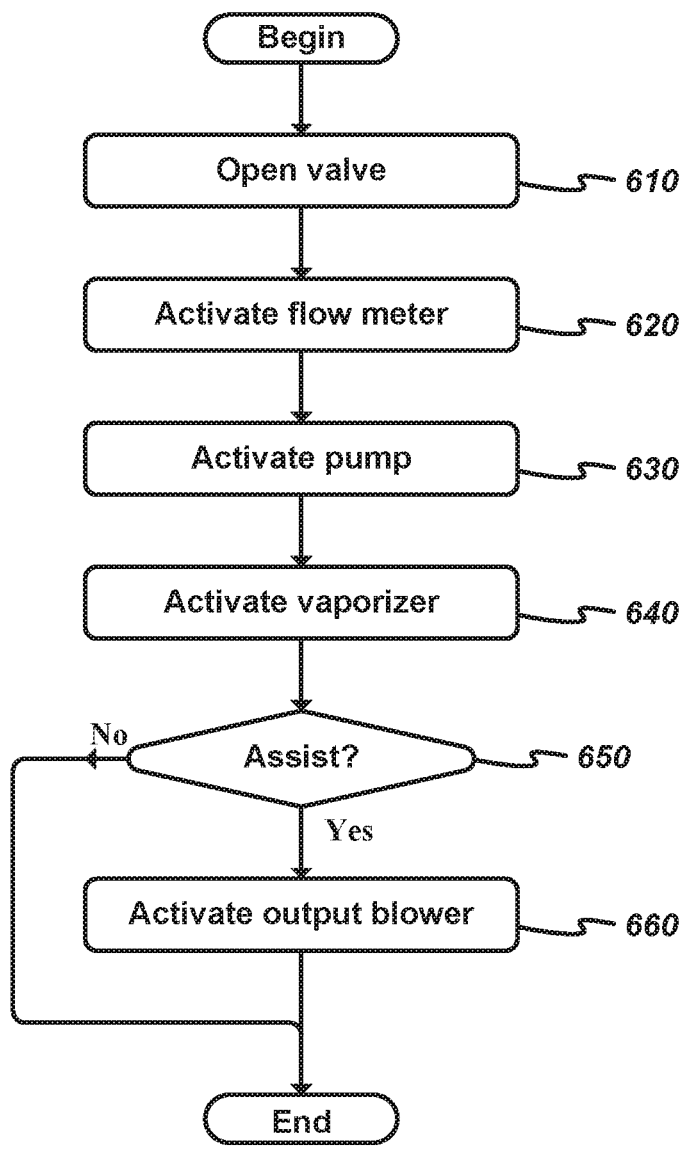
FIG. 6 illustrates a flow chart of an exemplary process that activates dosing using the inhaler device of FIG. 1.

FIG. 6 illustrates a flow chart of an exemplary process 600 that activates dosing using the inhaler device 100. Such a process may be executed by the inhaler device 100 in some embodiments. The process may be performed, for instance, as operation 540 described above.

As shown, process 600 may open (at 610) a cartridge valve such as valve 160. Next, the process may activate (at 620) a flow meter such as meter 165 (and/or other appropriate measurement resource such as a timer or counter).

Process 600 may then activate (at 630) a pump such as pump 170. Next, the process may activate (at 640) a vaporizer or atomizer such as vaporizer 175. The process may then determine (at 650) whether an assist should be provided by a resource such as output blower 180. Such a determination may be made based on various relevant criteria (e.g., substance attributes, cartridge attributes, user attributes and/or selections, etc.).

If the process determines (at 650) that no assist is needed, the process may end. If the process determines (at 650) that assist is needed, the process may activate (at 660) the output blower 180 or other appropriate resource and then may end.

Figure 7:
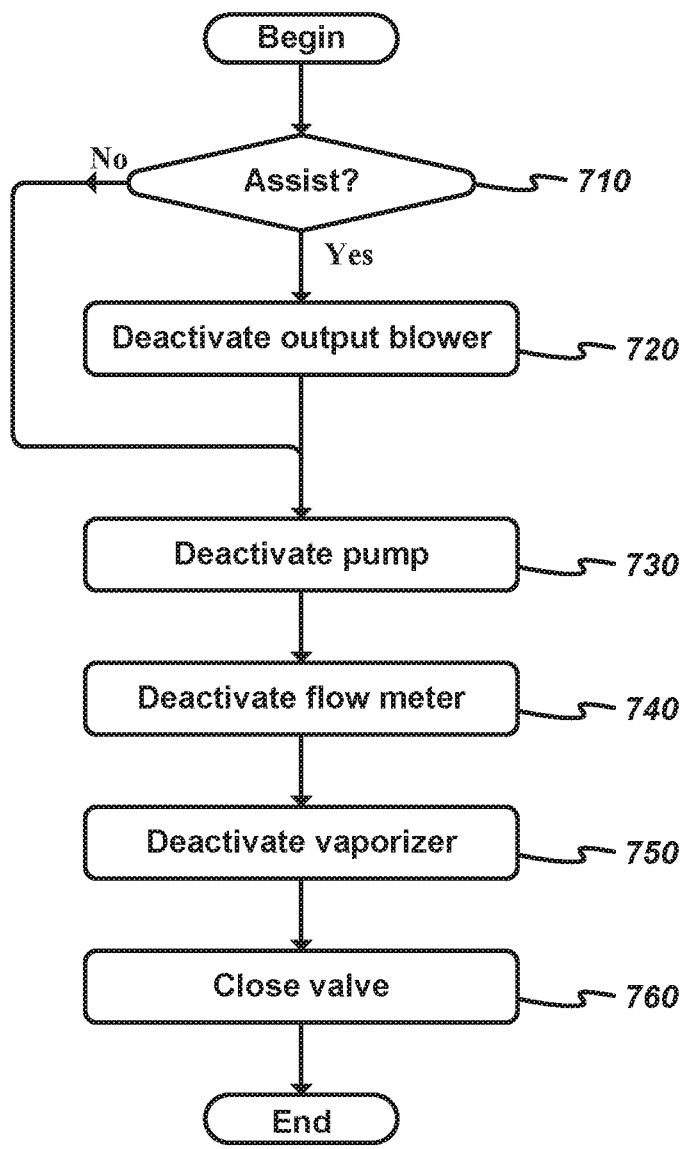
FIG. 7 illustrates a flow chart of an exemplary process that deactivates dosing using the inhaler device of FIG. 1.

FIG. 7 illustrates a flow chart of an exemplary process 700 that deactivates dosing using the inhaler device 100. Such a process may be executed by the inhaler device 100 in some embodiments. The process may be performed, for instance, as operation 570 described above.

As shown, process 700 may determine (at 710) whether assist has been activated. Such a determination may be made in various appropriate ways (e.g., by polling a state of the output blower 180). If the process determines (at 710) that assist is active, the process may deactivate (at 720) the output blower 180 or other appropriate resource. After deactivating (at 720) the output blower or after determining (at 710) that assist was not active, the process may deactivate (at 730) the pump 170 or other appropriate resource.

Next, the process may deactivate (at 740) the flow meter 165 or other appropriate measurement resource. Process 700 may then deactivate (at 750) the vaporizer 175, close (at 760) the valve 160, and then may end.

Different embodiments may deactivate the components in different orders depending on various relevant factors. For instance, a heating element associated with the vaporizer 175 or cartridge 155 may be deactivated before the output blower 180 is deactivated. As another example, the valve 160 may be closed before blower 180 is deactivated such that all vaporized substance is cleared from the flow pathway 150.

Figure 8:
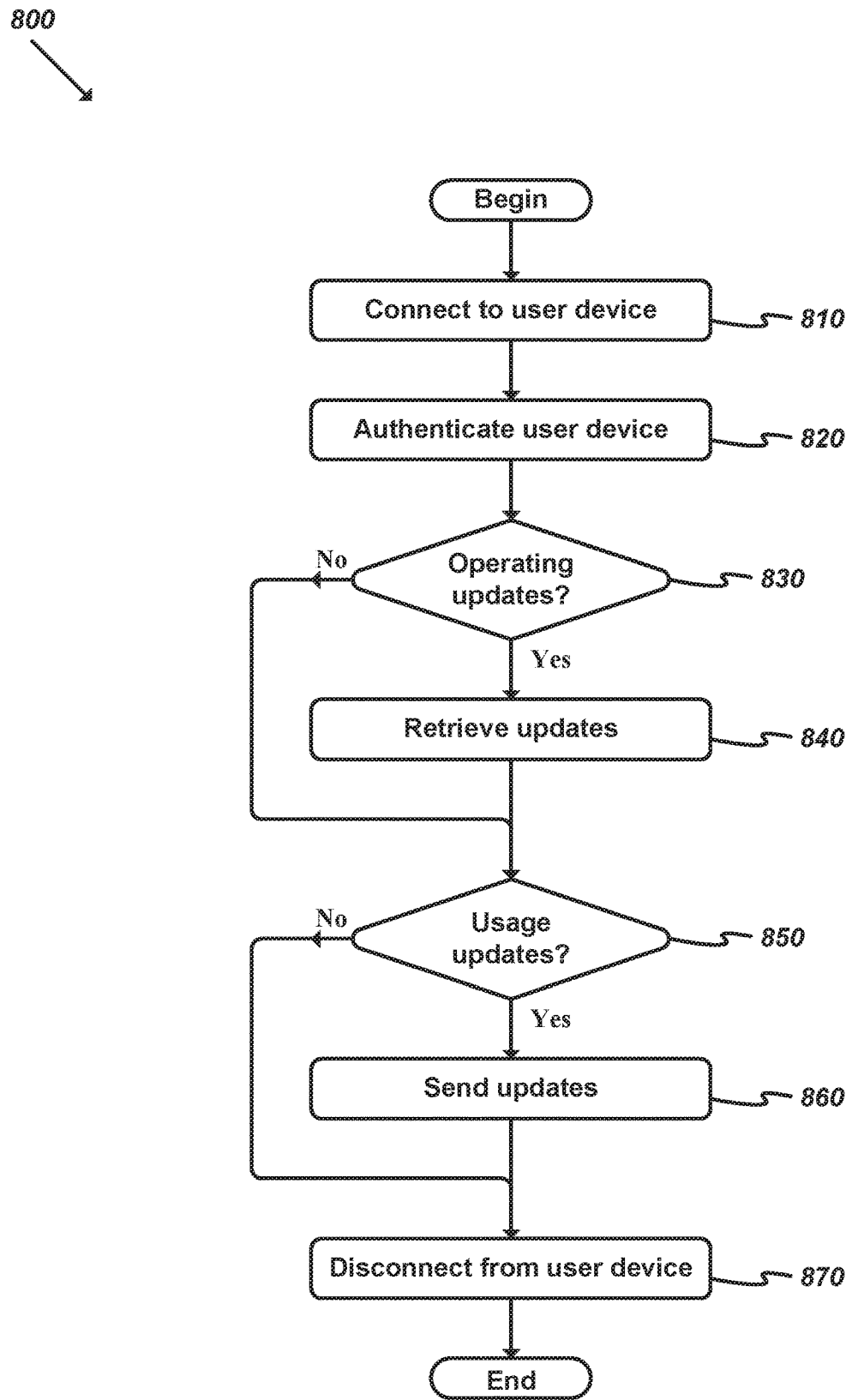
FIG. 8 illustrates a flow chart of an exemplary process that provides communication between the inhaler device of FIG. 1 and a user device.

FIG. 8 illustrates a flow chart of an exemplary process 800 that provides communication between the inhaler device 100 and a user device. Such a process may be executed by the inhaler device 100 in some embodiments. A complementary process may be executed by a device such as user device 210. The process may begin, for instance, when the inhaler device 100 is communicatively coupled to the user device 210.

As shown, the process may connect (at 810) the inhaler 100 to a user device such as device 210. The connection may be via a wired or wireless communication channel. Next, the process may authenticate (at 820) the user device. Such authentication may be based on various relevant criteria (e.g., entry of a PIN or password, facial or fingerprint scanning, verifying identifying information related to the device, etc.). For instance, in some embodiments, each user may have a list of associated inhaler devices 100, user devices 210, etc. Identifying information (e.g., MAC address, serial number, etc.) for authorized devices may be stored at the inhaler 100 and/or may be accessed via various external resources such as user device 210, server 220, or storage 230.

If the device is unable to be authenticated (at 820), a device authentication process may be executed. Such a process may collect the user device information, user information, password or PIN information, etc. and associate a user device 210 to an inhaler 100. The device authentication process may require a physical connection between the inhaler 100 and user device 210 (and/or other appropriate security measures, such as requiring a password or code included in the inhaler packaging). Such authentication or association may include registration via a server 220 or other online resource. A user may be able to associate multiple user devices 210 with a single inhaler 100 or multiple inhalers with a single user device 210.

In some scenarios, even non-authenticated user devices 210 may be able to connect to an inhaler 100 without authentication. For example, a non-authenticated device 210 may be able to connect and modify various settings (e.g., disable blower fan, adjust heat setting, etc.) but may not be able to access usage data or user information.

After authenticating (at 820) a user device 210, the process may determine (at 830) whether there are any operating updates. Such a determination may be made in various appropriate ways. For instance, the inhaler may send a request to a server 220 or storage 230 for the latest version of software or other data available for use by the inhaler 100. Such a request may be sent via the user device 210. The user device and/or inhaler 100 may likewise identify the version of software or data stored on the inhaler (and/or compare instantiations to identify any differences) and determine (at 830) that there are operating updates when there is a difference between the instantiations or between the versions. Some embodiments may identify a time associated with the most recent update and determine (at 830) that there are operating updates when a specified time period has passed since the most recent update.

If the process determines (at 830) that there are operating updates, the process may retrieve (at 840) the updates. Such updates may be retrieved from a resource such as server 220 or storage 230 and may be retrieved via the user device 210.

The updates may include software updates (e.g., firmware, interfaces, etc.) and/or parameter updates (e.g., operation settings, default values, etc.).

Such operating updates may also include user updates. For instance, after connecting the inhaler 100 to a user device 210, a user device application of some embodiments may be launched. The user device application may include various UI elements that may allow a user to adjust settings, review usage history, etc. Such user updates may include initial device setup and registration, creation or association of user accounts, enabling or disabling of data sharing, etc.

After retrieving (at 840) the updates or after determining (at 830) that there are no operating updates, the process may determine (at 850) whether there are usage updates. Such a determination may be made in various appropriate ways. For instance, a timestamp of the most recent usage session may be compared to a timestamp of the most recent uploaded session. As another example, the process may determine (at 850) that there are usage updates if a specified time period has passed since the last updates (where such updates may also indicate no use during the specified time period).

If the process determines (at 850) that there are usage updates, the process may send (at 860) the updates to an external resource such as a user device 210, server 220, storage 230, etc. Such updates may be sent via the user device 210.

After sending (at 860) the updates or after determining (at 850) that there are no usage updates, the process may disconnect (at 870) from the user device 210 and then may end.

Figure 9:
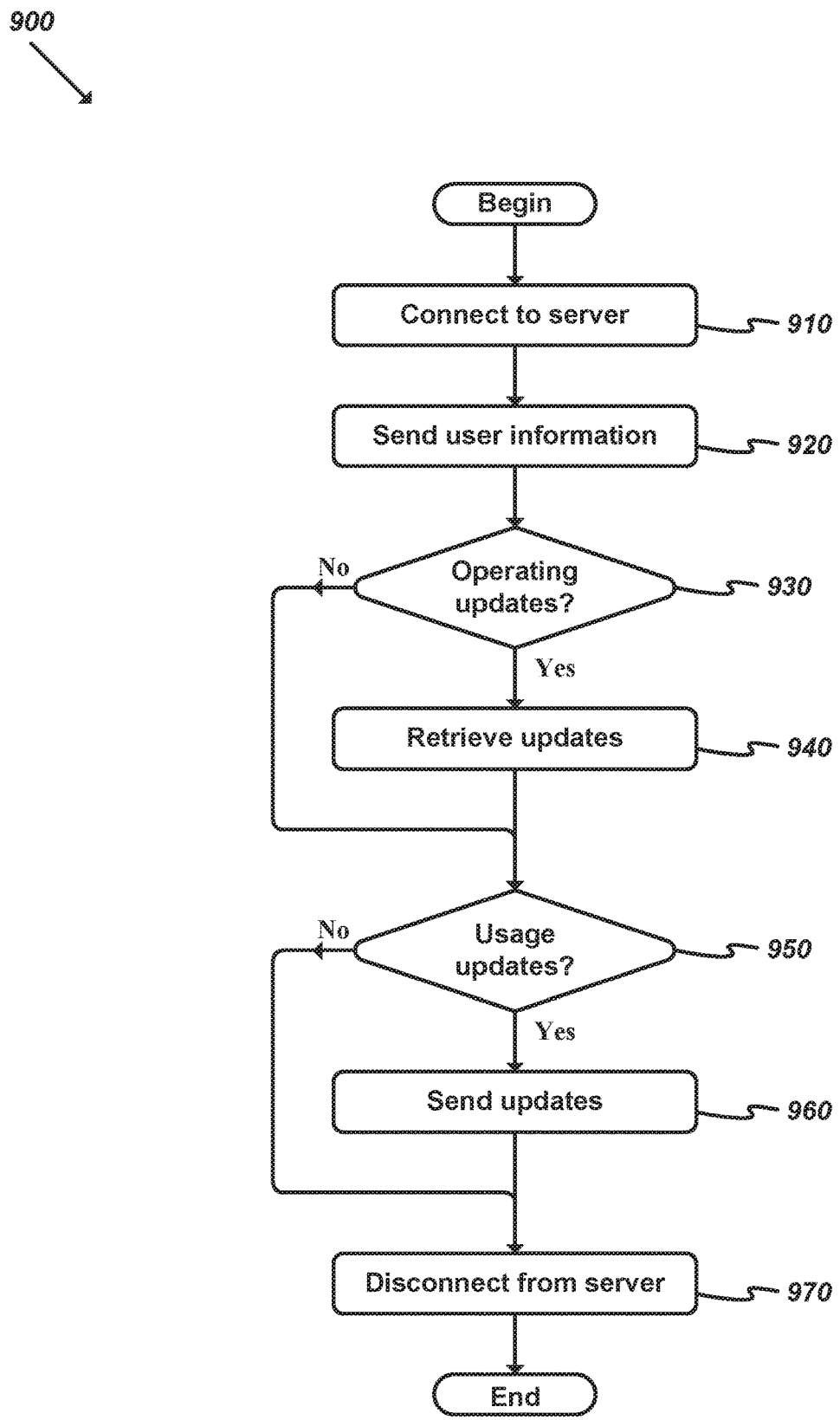
FIG. 9 illustrates a flow chart of an exemplary process that provides communication between a user device and a server of some embodiments.

FIG. 9 illustrates a flow chart of an exemplary process 900 that provides communication between a user device and a server of some embodiments. Such a process may be executed by the user device 210 in some embodiments. Alternatively, the process may be executed by an inhaler 100 that is able to communicate with a server or other online resource. A complementary process may be executed by a device such as server 220. The process may begin, for instance, when an application of some embodiments is launched, when the user device 210 is communicatively coupled to the server 220, etc.

As shown, the process may connect (at 0910) to a server such as server 220. Alternatively, the process may connect to a resource such as storage 230 via an API or other appropriate interface. In addition, the inhaler 100 and/or user device 210 may execute applications of some embodiments.

Next, the process may send (at 920) user information. Such information may include, for instance, identifying information such as a username, authenticating information such as a password, and/or other appropriate user information. In addition, such information may include, for instance, inhaler device identifying information (e.g., serial number), user device identifying information (e.g., MAC address, serial number, etc.), current versions of software or operating parameters, timestamp of last updates, timestamp of last inhaler device 0100 use, etc.

The user device 210 may be authenticated in various appropriate ways (e.g., by comparing identifying information such as MAC address to a list of authorized devices associated with a user account). If the user device has not previously been authorized, an error or warning message may be sent and the process may end.

In addition to sending (at 920) user information, the process may retrieve information from the server or other resource. Such information may include, for instance, a latest version of software and/or operating parameters, timestamp of last connection, etc.

After sending (at 920) user information and/or retrieving server information, the process may determine (at 930) whether there are any operating updates. Such a determination may be made in various appropriate ways. For instance, the versions of installed software may be compared to versions of available software. Some embodiments may identify a time associated with the most recent update and determine (at 930) that there are operating updates when a specified time period has passed since the most recent update.

If the process determines (at 930) that there are operating updates, the process may retrieve (at 940) the updates. Such updates may be retrieved from a resource such as server 220 or storage 230 and may be retrieved via the user device 210. The updates may include software updates (e.g., firmware, interfaces, etc.) and/or parameter updates (e.g., operation settings, default values, etc.). Such updates may include updates to the applications executed by the inhaler 100 and/or user device 210 in some embodiments. In addition to updates, initial installations may be performed in a similar manner.

Such operating updates may also include user updates. For instance, after connecting the inhaler 100 to a user device 210, a user device application of some embodiments may be launched. The user device application may include various UI elements that may allow a user to adjust settings, review usage history, etc. Such user updates may include initial device setup and registration, creation or association of user accounts, enabling or disabling of data sharing, etc.

After retrieving (at 940) the updates or after determining (at 930) that there are no operating updates, the process may determine (at 950) whether there are usage updates. Such a determination may be made in various appropriate ways. For instance, a timestamp of the most recent usage session may be compared to a timestamp of the most recent uploaded session. As another example, the process may determine (at 950) that there are usage updates if a specified time period has passed since the last updates (where such updates may also indicate no use during the specified time period). In some embodiments, usage information may be uploaded from the inhaler 100 to a device such as user device 210 using a process such as process 800. The usage information may be stored at the user device until a process such as process 900 is executed.

If the process determines (at 950) that there are usage updates, the process may send (at 960) the updates to an external resource such as server 220, storage 230, etc.

After sending (at 960) the updates or after determining (at 950) that there are no usage updates, the process may disconnect (at 970) from the server 220 and then may end.

One of ordinary skill in the art will recognize that processes 300-900 may be performed in various different ways without departing from the scope of the disclosure. For instance, the listed operations may be performed in different orders than shown. In addition, some embodiments may include additional operations and/or omit one or more listed operations. Operations and/or sets of operations may be performed iteratively and/or based on various performance criteria. Each process may be divided into multiple sub-processes and/or included as part of a larger macro process.

IV. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

Figure 10:
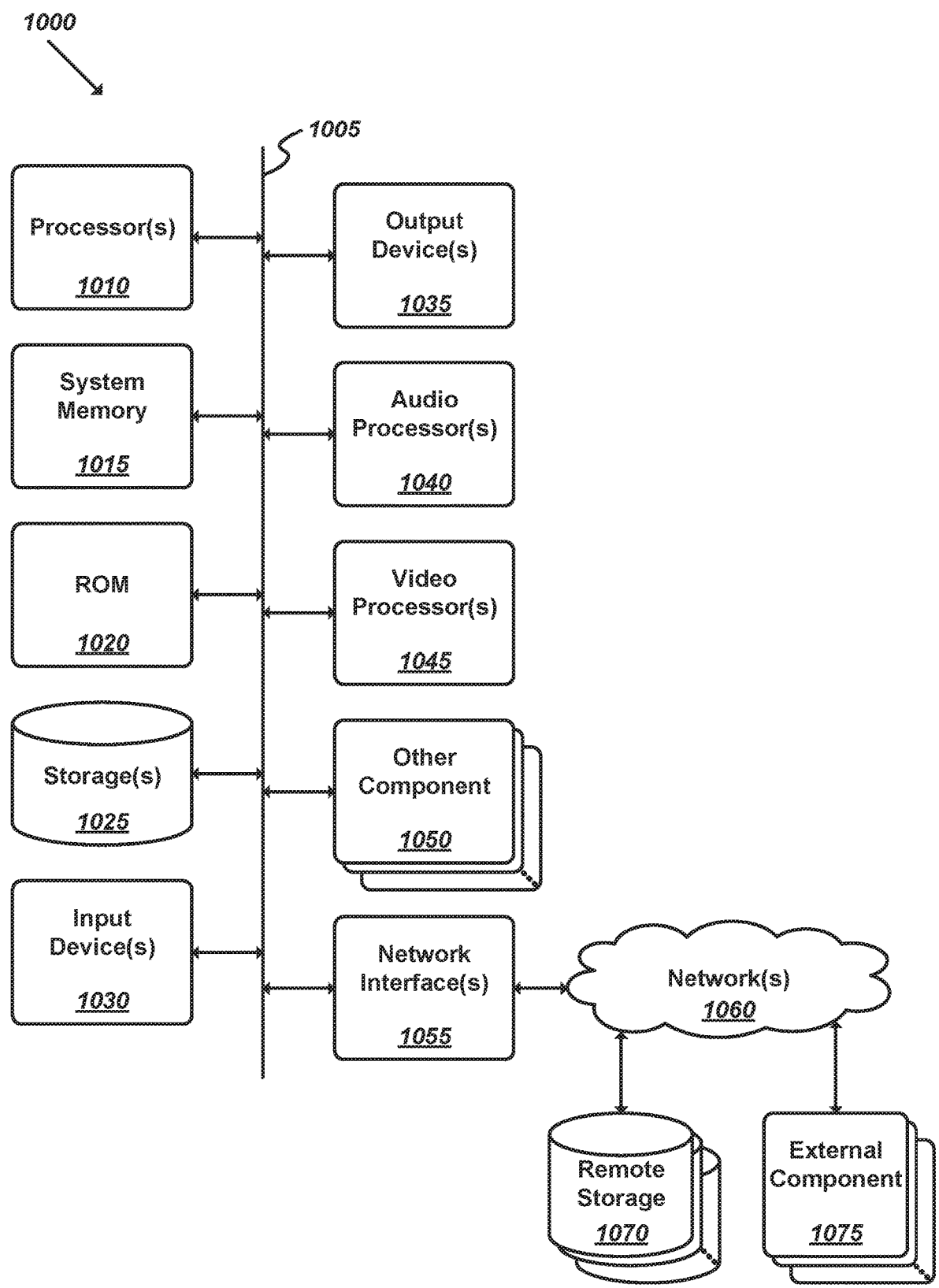
FIG. 10 illustrates a schematic block diagram of an exemplary computer system used to implement some embodiments.

FIG. 10 illustrates a schematic block diagram of an exemplary computer system 1000 used to implement some embodiments. For example, the device and system described above in reference to FIG. 1 and FIG. 2 may be at least partially implemented using computer system 1000. As another example, the processes described in reference to FIG. 3-FIG. 9 may be at least partially implemented using sets of instructions that are executed using computer system 1000.

Computer system 1000 may be implemented using various appropriate devices. For instance, the computer system may be implemented using one or more personal computers (PCs), servers, mobile devices (e.g., a smartphone), tablet devices, and/or any other appropriate devices. The various devices may work alone (e.g., the computer system may be implemented as a single PC) or in conjunction (e.g., some components of the computer system may be provided by a mobile device while other components are provided by a tablet device).

As shown, computer system 1000 may include at least one communication bus 1005, one or more processors 1010, a system memory 1015, a read-only memory (ROM) 1020, permanent storage devices 1025, input devices 1030, output devices 1035, audio processors 1040, video processors 1045, various other components 1050, and one or more network interfaces 1055.

Bus 1005 represents all communication pathways among the elements of computer system 1000. Such pathways may include wired, wireless, optical, and/or other appropriate communication pathways. For example, input devices 1030 and/or output devices 1035 may be coupled to the system 1000 using a wireless connection protocol or system.

The processor 1010 may, in order to execute the processes of some embodiments, retrieve instructions to execute and/or data to process from components such as system memory 1015, ROM 1020, and permanent storage device 1025. Such instructions and data may be passed over bus 1005.

System memory 1015 may be a volatile read-and-write memory, such as a random access memory (RAM). The system memory may store some of the instructions and data that the processor uses at runtime. The sets of instructions and/or data used to implement some embodiments may be stored in the system memory 1015, the permanent storage device 1025, and/or the read-only memory 1020. ROM 1020 may store static data and instructions that may be used by processor 1010 and/or other elements of the computer system.

Permanent storage device 1025 may be a read-and-write memory device. The permanent storage device may be a non-volatile memory unit that stores instructions and data even when computer system 1000 is off or unpowered. Computer system 1000 may use a removable storage device and/or a remote storage device as the permanent storage device.

Input devices 1030 may enable a user to communicate information to the computer system and/or manipulate various operations of the system. The input devices may include keyboards, cursor control devices, audio input devices and/or video input devices. Output devices 1035 may include printers, displays, audio devices, etc. Some or all of the input and/or output devices may be wirelessly or optically connected to the computer system 1000.

Audio processor 1040 may process and/or generate audio data and/or instructions. The audio processor may be able to receive audio data from an input device 1030 such as a microphone. The audio processor 1040 may be able to provide audio data to output devices 1040 such as a set of speakers. The audio data may include digital information and/or analog signals. The audio processor 1040 may be able to analyze and/or otherwise evaluate audio data (e.g., by determining qualities such as signal to noise ratio, dynamic range, etc.). In addition, the audio processor may perform various audio processing functions (e.g., equalization, compression, etc.).

The video processor 1045 (or graphics processing unit) may process and/or generate video data and/or instructions. The video processor may be able to receive video data from an input device 1030 such as a camera. The video processor 1045 may be able to provide video data to an output device 1040 such as a display. The video data may include digital information and/or analog signals. The video processor 1045 may be able to analyze and/or otherwise evaluate video data (e.g., by determining qualities such as resolution, frame rate, etc.). In addition, the video processor may perform various video processing functions (e.g., contrast adjustment or normalization, color adjustment, etc.). Furthermore, the video processor may be able to render graphic elements and/or video.

Other components 1050 may perform various other functions including providing storage, interfacing with external systems or components, etc.

Finally, as shown in FIG. 10, computer system 1000 may include one or more network interfaces 1055 that are able to connect to one or more networks 1060. For example, computer system 1000 may be coupled to a web server on the Internet such that a web browser executing on computer system 1000 may interact with the web server as a user interacts with an interface that operates in the web browser. Computer system 1000 may be able to access one or more remote storages 1070 and one or more external components 1075 through the network interface 1055 and network 1060. The network interface(s) 1055 may include one or more application programming interfaces (APIs) that may allow the computer system 1000 to access remote systems and/or storages and also may allow remote systems and/or storages to access computer system 1000 (or elements thereof).

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

It should be recognized by one of ordinary skill in the art that any or all of the components of computer system 1000 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments and modifications may be made without departing from the scope of the disclosure as defined by the following claims.

We claim:

1. A smart inhaler device comprising:
a flow pathway comprising a cartridge receptacle that houses a cartridge, flow meter, pump, and vaporizer;
a wireless communication module;
at least one sensor that captures identifying information related to the cartridge;
a fingerprint scanner that captures a fingerprint;
a security module that:
  receives a prescription associated with a user;
  generates and stores a prescription reference file, the prescription reference file comprising:
    a captured reference fingerprint associated with the user and
    a prescription cartridge serial number associated with the cartridge and with the prescription; and
  compares the captured fingerprint captured by the fingerprint scanner to the captured reference fingerprint associated with the user, wherein no substance is dispensed from the smart inhaler device unless:
    at least a portion of the captured reference fingerprint matches at least a portion of the captured fingerprint; and
    the identifying information related to the cartridge comprises a unique cartridge serial number that matches the prescription cartridge serial number; and
a storage that collects usage information related to the smart inhaler device, wherein the usage information comprises a quantity measured by the flow meter, identifying information related to the cartridge, a number of doses administered, and a timestamp associated with each administered dose.

2. The smart inhaler device of claim 1, wherein the flow pathway further comprises an output blower that assists a vaporized substance along the flow pathway from the vaporizer to a mouth piece.

3. The smart inhaler device of claim 1, wherein the at least one sensor comprises a camera and the identifying information comprises a graphic code.

4. The smart inhaler device of claim 1, wherein the at least one sensor comprises a near field communication (NFC) receiver and the identifying information comprises an NFC tag.

5. The smart inhaler device of claim 1, wherein the cartridge comprises a substance associated with the prescription, the prescription comprising at least one of a specified dose amount, dose frequency, maximum dose, maximum dose over time, and total usage period.

6. The smart inhaler device of claim 1, wherein a metered dose is provided by using the flow meter to measure an amount of substance that is vaporized.

7. The smart inhaler device of claim 1, wherein the cartridge comprises a storage cavity that houses a substance comprising at least one of an opioid, cannabinoid, and nicotine-based solution.

8. The smart inhaler device of claim 1, wherein the wireless communication module communicatively couples the smart inhaler device to an external device, the external device comprising at least one of a smartphone, tablet, personal computer, server, and storage.

* * * * *